US006979541B1

(12) United States Patent
Pont-Kingdon et al.

(10) Patent No.: US 6,979,541 B1
(45) Date of Patent: Dec. 27, 2005

(54) METHODS FOR IDENTIFYING CHROMOSOMAL ANEUPLOIDY

(75) Inventors: Genevieve Pont-Kingdon, Salt Lake City, UT (US); Elaine Lyon, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 405 days.

(21) Appl. No.: 10/206,406

(22) Filed: Jul. 26, 2002

Related U.S. Application Data

(60) Provisional application No. 60/307,969, filed on Jul. 26, 2001.

(51) Int. Cl.[7] .......................... C07H 21/04; C12Q 1/68
(52) U.S. Cl. ........................ 435/6; 435/91.1; 435/91.2; 536/23.1
(58) Field of Search .......................... 435/6, 91.1, 91.2; 536/23.1

(56) References Cited

U.S. PATENT DOCUMENTS

| | | | |
|---|---|---|---|
| 5,455,175 A | | 10/1995 | Wittwer et al. |
| 5,888,740 A | * | 3/1999 | Han ................................ 435/6 |
| 5,935,522 A | | 8/1999 | Swerdlow et al. |
| 5,976,790 A | | 11/1999 | Pinkel et al. |
| 6,140,054 A | | 10/2000 | Wittwer et al. |
| 6,174,670 B1 | | 1/2001 | Wittwer et al. |
| 6,197,520 B1 | | 3/2001 | Wittwer et al. |
| 6,232,079 B1 | | 5/2001 | Wittwer et al. |
| 6,254,514 B1 | | 7/2001 | Maresh et al. |
| 6,265,546 B1 | * | 7/2001 | Cohen et al. ................ 530/350 |
| 6,303,305 B1 | | 10/2001 | Wittwer et al. |
| 6,387,621 B1 | | 5/2002 | Wittwer |
| 6,391,551 B1 | * | 5/2002 | Shultz et al. .................. 435/6 |
| 6,410,231 B1 | * | 6/2002 | Arnold et al. ................. 435/6 |
| 6,506,568 B2 | * | 1/2003 | Shriver et al. ................. 435/6 |

OTHER PUBLICATIONS

Ohira et al. "A 1.6Mb P1-based physical map of the down syndrome region on chromosome 21" Genomics, VOl. 33, pp. 65-74, 1996.*
Clara Ruiz-Ponte, et al.,*Rapid Real-Time Fluorescent PCR Gene Dosage Test for the Diagnosis of DNA Duplications and Deletions*, Clinical Chemistry 46:10, 1574-1582 (2000).
Ian Findlay, et al., *Rapid Trisomy Diagnosis (21, 18, and 13) Using Fluorescent PCR and Short Tandem Repeats: Applications for Prenatal Diagnosis and Preimplantation Genetic Diagnosis*, Journal of Assisted Reproduction and Genetics, vol. 15, No. 5, 1998.
Elaine Lyon, et al., *Quantification of HER2/neu Gene Amplification by Competitive PCR Using Fluorescent Melting Curve Analysis*, Clinical Chemistry 47:5 844-851 (2001).
Elain Lyon *Mutation Detection Using Fluorescent Hybridization Probes and Melting Curve Analysis*, Exp. Rev. Mol. Diagn. 1 (1), 2001.

* cited by examiner

*Primary Examiner*—Jeanine A. Goldberg
(74) *Attorney, Agent, or Firm*—Thorpe North & Western, L.L.P.

(57) ABSTRACT

Methods are disclosed for identifying chromosomal aneuploidy using heterozygous SNPs in a melting curve analysis. In one aspect, a panel of SNPs may be used. The heterozygous nature of the SNPs may in some aspects, act as an internal control for the melting curve analysis, and alleviate the need for external controls or competitors. In another aspect, each of the SNP in the panel may have a heterozygocity index of greater than about 30%. While a number of aneuploidies may be identified using the disclosed methods, in one aspect, the chromosomal aneuploidy identified may be trisomy 21.

5 Claims, 4 Drawing Sheets

WIAF-2643
n=24 (trisomic), n=19 (non-trisomic)

WIAF-899
n=24 (trisomic), n=19 (non-trisomic)

WIAF-2215
n=18 (trisomic), n=11 (non-trisomic)

WIAF-1538
n=24 (trisomic), n=14 (non-trisomic)

METHODS FOR IDENTIFYING CHROMOSOMAL ANEUPLOIDY

PRIORITY DATA

This application claims priority to U.S. Provisional Patent Application Ser. No. 60/307,969, filed on Jul. 26, 2001, which is incorporated herein by reference in its entirety.

FIELD OF THE INVENTION

The present invention relates to methods for quantifying alleles presence in a biological sample in order to identify DNA dosage defects, such as aneuploidy. More particularly, the present invention involves using a panel of specifically selected single nucleotide polymorphisms (SNPs) in connection with fluorescent hybridization probes and a melting curve analysis for allele quantification.

BACKGROUND OF THE INVENTION

Proper DNA dosage has been recognized as essential for normal cellular development and function. A wide variety of specific DNA dosage defects are known, ranging from single gene duplication to gene amplification and partial chromosomal duplication to whole chromosomal additions, each of which typically results in a number of adverse consequences. For example, gene duplication and amplification have been positively linked to cellular oncogenic transformation, while chromosomal aneuploidies have been linked to serious birth defects.

One type of aneuploidy known to cause Down Syndrome is the trisomy of chromosome 21. Down Syndrome is one of the most common causes of mental retardation and is observed in approximately 1/800 live births. Although most Down Syndrome cases are due to an extra chromosome, partial duplications of a critical region on chromosome 21 in the DSCR (i.e. Down Syndrome Critical Region) can also cause clinical symptoms. Other trisomies compatible with life besides trisomy 21 include trisomy 13, trisomy 18, and various X and Y chromosome trisomies that lead to conditions such as Turner's Syndrome and Klinfelter's Syndrome.

The risk of child birth defects, including Down Syndrome, increases with a mother's age. To this end, prenatal detection of trisomies has been made available to women with advanced maternal age (over age 35). Moreover, defect testing is typically performed on pregnant women who have previously given birth to children with chromosomal abnormalities, and also to confirm fetus ultrasound image testing that indicates the possibility of Down Syndrome.

The conventional diagnosis of Down Syndrome is by chromosome karyotype. A karyotype shows the complete chromosome complement in a cell. Karyotypes detect any chromosomal aneuploidy (i.e. numerical abnormality) as well as structural chromosomal rearrangements. Sample types for chromosomal analysis include cultured amniotic cells or chorionic villi. Postnatal samples typically are peripheral whole blood. The strength of karyotype testing is a definitive diagnosis of aneuploidy and the ability to detect any chromosomal abnormality such as rearrangements and large chromosomal deletions and insertions. However, several drawbacks to the procedure exist, such as the necessity to culture cells, which in the case of prenatal diagnosis may take up to 2 weeks. Moreover, as the culturing process requires viable cells, it is unable to test a product of conception that has not yet reached certain developmental stages, such as an embryo or fetus. Further, karyotyping may not be able to detect small duplications in the Down's syndrome critical region.

One molecular cytogenetic method that has been used for faster detection of trisomies is the technique know as fluorescent in situ hybridization (FISH). FISH employs a system of fluorescent hybridization probes and antibodies to directly visualize the location of a target nucleotide sequence in a DNA molecule. See, *In Situ Hybridization. A Practical Approach.* Edited by D. G. Wilkinson, IRL Press, Oxford University Press (1994). While FISH does offer several advantages in the detection of trisomies over karyotyping, it is still quite time consuming, requires intact cells, a fluorescent microscope, and technical expertise in the use and operation of such equipment. Furthermore, FISH may not detect small duplications, such as those recited above in the DSCR of chromosome 21.

Another method for detecting trisomies has focused on the use of short tandem repeats (STRs). See, Findlay et al. *Rapid Trisomy Diagnosis (21, 18, and 13) Using Fluorescent PCR and Short Tandem Repeats. Journal of Assistant Reproduction and Genetics.* Vol. 15, No. 5. p 266–275. STRs are 2 to 5 nucleotides repeated a variable number of times. STRs are amplified by PCR and are separated by size on a sequencing gel. The band intensity is used to determine the number of copies of each allele. This technique, although suitable for simultaneous detection of a number of trisomies has not been widely implemented in clinical laboratories. Further, this techniques continues to suffer from a variety of the above recited disadvantages, as well as others, such as a limited number of STR loci compared to SNP loci on a chromosome.

A recent device that has been used for the quantification of gene dosage, as well as the identification of mutations and other genetic phenomena is marketed under the trade name LightCycler® by Roche Diagnostics, GMBH (Penzberg, Del.). Essentially, this instrument couples a thermocycler for polymerase chain reaction (PCR) amplification of materials with a fluorescence detector that allows for the real-time monitoring of amplification products. Specific examples of various instrument configurations, reagents for use therein, and uses therefor are found in U.S. Pat. Nos. 5,455,175, 5,935,522, 6,140,054, 6,174,670, 6,197,520,6,232,079, 6,254,514, 6,303,305, and 6,387,621, each of which is incorporated herein by reference. Further, specific methods of detecting certain DNA Duplications and Deletions using the LightCycler® have been disclosed by Ruiz-Ponte et al. in an article entitled *Rapid Real-Time Fluorescent PCR Gene Dosage Test for the Diagnosis of DNA Duplications and Deletions*, which is incorporated herein by reference. See, Ruiz-Ponte et al., *Clinical Chemistry*, 46:10, 1574–1582 (2000). Moreover, specific methods of detecting certain mutations using the LightCycler® is disclosed by Elaine Lyon in an article entitled *Mutation Detection Using Fluorescent Hybridization Probes and Melting Curve Analysis*, which is also incorporated herein by reference. See, Lyon, *Exp. Rev. Mol. Diagn.* 1 (1), (2001).

Despite the successful implementation of the above-recited methods and protocols for their respective purposes, the afore-mentioned disadvantages, as well as others, present needs that are not met by the current state of the art. Therefore, additional methods for the quantification of alleles and resultant detection of trisomic conditions, especially of chromosome 21, continue to be sought through ongoing research and development efforts.

SUMMARY OF THE INVENTION

Accordingly, the present invention provides methods of detecting chromosomal aneuploidies, such as trisomy 13, 18, and 21 using SNPs in a in a real-time PCR and melting curve analysis. The methods of the present invention are also capable of detecting partial chromosomal duplication. As a result, the present methods can more accurately define the Down Syndrome critical region in cases of partial chromosome duplication. In one aspect, the method of the present invention may include the steps of: a) providing a biological sample containing alleles that are heterozygous by at least a single nucleotide polymorphism (SNP); b) selecting a panel of target SNPs; c) hybridizing target SNPs contained in the heterozygous alleles with fluorescent hybridization probes; d) measuring hybridization as a function of fluorescence and temperature; and e) quantifying hybridization as a ratio of heterozygous alleles present in the biological sample. In one aspect of the invention, the chromosomal aneuploidy detected may be trisomy 21.

The SNPs used in the panel may be selected from a number of currently known SNPs. However, in one aspect of the invention, the target SNPs may each have a heterozygocity index of greater than about 30%. In another aspect, each of the target SNPs may have a heterozygocity index of greater than about 50%. In yet another aspect, the panel of SNPs may provide at least one heterozygous loci in at least about 95% of a random population. Further, while the panel of SNPs may include any number of SNPs, in one aspect, the panel may include at least 3 different SNPs. In a further aspect, the panel may include at least 4 SNPs. In another aspect, the panel may include at least 6 different SNPs. In yet another aspect, the panel may include more than 6 different SNPs.

As will be recognized by those of ordinary skill in the art, the expected loci for the target SNPs used in the panel of the present invention are determined as a function of the specific aneuploidy to be tested. Therefore, if testing for aneuploidy of chromosome 13, at least one, or preferably more, of the target SNPs selected to be in the panel will have loci on chromosome 13. Likewise, if testing for aneuploidy of chromosome 21, at least one, or preferably more, of the target SNPs selected to be in the panel will have loci on chromosome 21. In one aspect of the invention, the panel of target SNPs includes SNPs having loci on at least one chromosome selected from the group consisting essentially of: chromosome 13, chromosome 18, chromosome 21, chromosome X, chromosome Y, and combinations thereof. In an additional aspect of the invention, the panel of target SNPs may consist essentially of SNPs having loci on chromosome 21. Notably, such SNPs may include, or be further limited to, loci in the 21q22.1 to the 21q22.3 arm of chromosome 21.

For certain analysis, it may be desirable to utilize target SNPs in the panel which have loci in a broad distribution throughout a chromosome rather than in a single concentrated area thereof. In one aspect of the invention, the target SNPs in the panel may have loci distributed throughout a single chromosome in a manner sufficient to allow detection of chromosomal trisomy, partial trisomy, and chromosomal breakpoint locations. In another aspect, the loci distribution may be sufficient to distinguish between chromosomal trisomy and partial trisomy.

One advantage of using heterozygous alleles in the method of the present invention is that the heterozygocity of the alleles acts as an internal control for quantifying hybridization of the fluorescent probes used in the melting curve analysis. As a result, it is not necessary to employ artificial controls or other competitors in order to obtain a readable indication of allele number.

The biological sample used in the method of the present invention may be obtained from a wide variety of sources. By way of example without limitation, samples may be obtained from epithelium of the oral cavity, blood, hair, skin, saliva, and other bodily fluids. Additionally, the sample for a given analysis may be obtained from an individual displaying certain symptoms or conditions, for example, the sample may be obtained from a woman who is pregnant. In some cases, it is necessary to take the sample from a specific physiological portion of the individual displaying the symptoms, such as the amniotic fluid of a pregnant woman, in order to obtain the desired genetic material for analysis. Such sample targets can be readily determined by one of ordinary skill in the art depending on the test aneuploidy being tested.

The biological sample may also be taken at various times in the development of an organism in order to obtain the desired genetic material. For example, a sample may be taken from a product of conception in various stages of development, such as a fertilized zygote, an embryo, or a fetus. Moreover, the ability to take samples from such products of conception allows samples to be taken from in vitro or aborted products, which has not generally been possible with the techniques of the prior art.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION OF THE INVENTION

Figure 1:
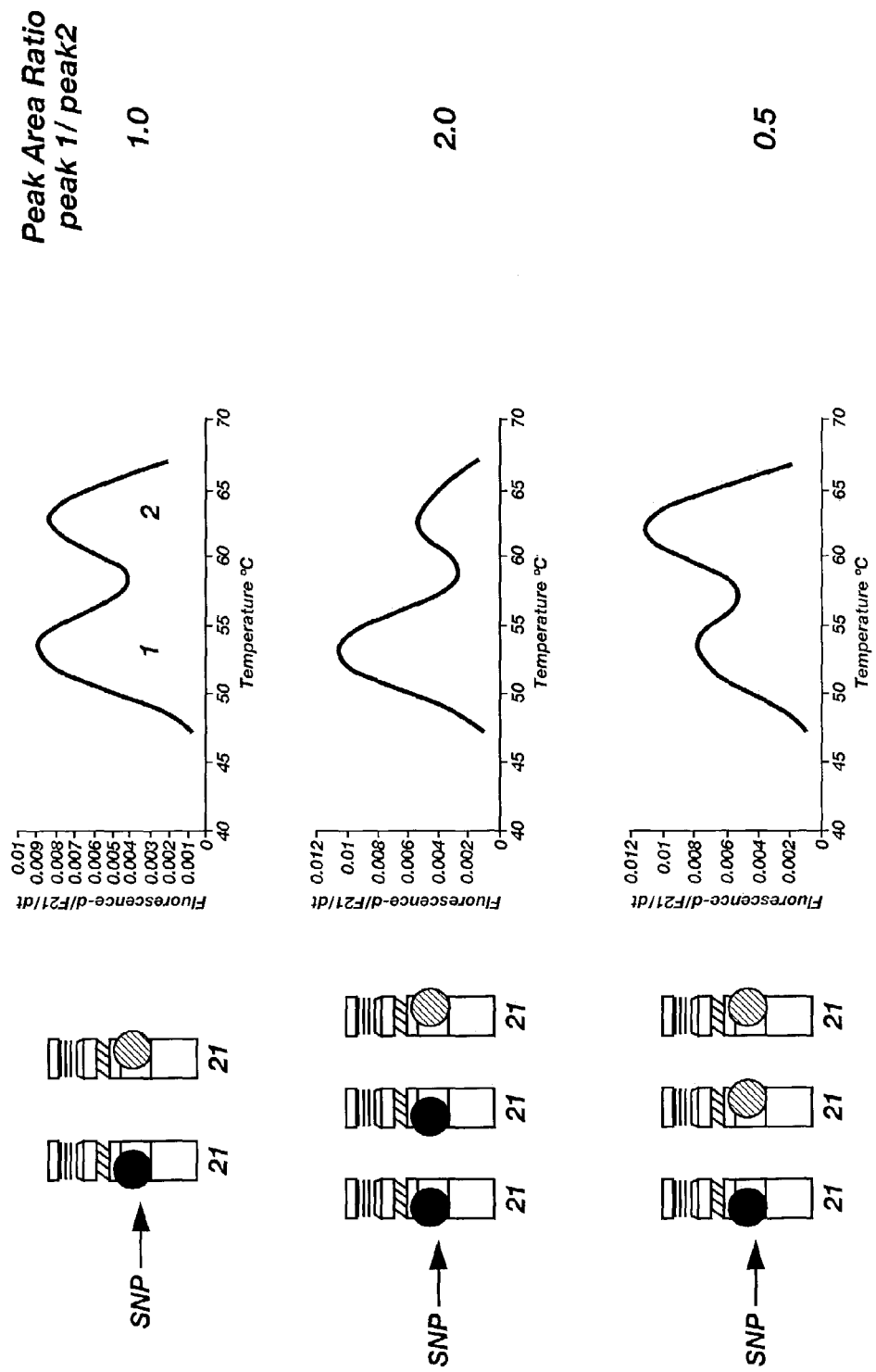
FIG. 1 depicts the general principle of the assay of the present invention.

Before the present methods are disclosed and described, it is to be understood that this invention is not limited to the particular configurations discussed, as process steps and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Therefore, "a" probe includes reference to one or more of such probes, "an allele" includes reference to one or more alleles, and "the sample source" refers to one or more of such sample sources.

Definitions

In describing and claiming the present invention, the following terminology will be used.

As used herein, "allele" refers to one of an alternative version of a gene or DNA marker. Individuals typically have two alleles (i.e. a pair) for a given trait, one allele inherited from each parent.

As used herein, "homozygous" refers to the presence of a pair of alleles having identical nucleotide sequences at corresponding chromosomal loci.

As used herein, "heterozygous" refers to the presence of a pair of alleles having different nucleotide sequences at corresponding chromosomal loci.

As used herein "single nucleotide polymorphism" or "SNP" refers to a single nucleotide difference between nucleotide sequences at corresponding chromosomal loci in a pair of alleles, that occurs naturally in a given population with a frequency that is greater than can be explained by recurrent mutation alone (typically greater than 1% of the population).

As used herein, "heterozygocity index" refers to the frequency with which a pair of alleles, rendered heterozygous by an SNP, appears in a random population.

As used herein, in the context of SNPs, a "panel" refers to a group of at least two or more target SNPs that have been specifically selected for use in a melting curve analysis. A number of criteria may be utilized in selecting specific SNPs for inclusion in the panel, such as the heterozygocity index of the SNP, the chromosome on which the SNP typically appears, and the specific results sought by the particular test (i.e., chromosome 21 trisomy, etc.).

As used herein, a "product of conception" refers to a cell or group of cells in any active or arrested stage of development, that was created by the union of male and female gametes.

As used herein, a "fertilized zygote" refers to a zygote that has been fertilized but not yet implanted in a uterus.

Concentrations, amounts, solubilities, ratios, and other numerical or statistical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 1% w/w to 10% w/w should be interpreted to include not only the explicitly recited concentration limits of 1% and 10%, but also to include individual concentrations within that range, as well as sub ranges such as 2% w/w, 3.5%–4.5% w/w, 4.1% w/w, 5% w/w, 8% w/w, etc. This same principle applies to ranges reciting only one numerical value. Furthermore, such an interpretation should apply regardless of the breadth of the range or the characteristics being described.

Invention

The present invention encompasses methods for the rapid detection of chromosomal aneuploidy via the quantification of alleles. Generally, allele quantification is carried out by providing a biological sample containing alleles made heterozygous by at least a single nucleotide polymorphism (SNP), and performing a melting curve analysis on the alleles. The quantification of the derivative melting curve then yields the ratio in which heterozygous alleles are present in the biological sample.

The basic equipment and accompanying methods used for such an analysis includes a thermocycler coupled to a fluorescence detector, as in the above-recited patents which are incorporated herein by reference. As indicated, one commercial example of this instrumentation is the LightCycler®. The basic analytical method employed by such instrumentation is to isolate target nucleotide strands from a crude biological sample and amplify such strands utilizing typical PCR reagents and ingredients, such as a TAQ polymerase. The amplified nucleotide strands are then hybridized at target areas to hybridization probes having fluorescent markers. Probes are designed so as to fluoresce while bound to the nucleotide strand, and cease fluorescing when they become denatured therefrom. An alternative design, based on fluorophores used, is for probes to fluoresce when denatured and lose fluorescence when bound to a nucleotide strand. A melting curve analysis is then performed by slowly raising the temperature of the PCR reaction mixture and measuring the temperatures at which fluorescence is lost or gained, depending on the probe design (i.e. the temperature at which the probes denature). These measurements are recorded, and a derivative curve is quantified which provides area information for the samples. This general process is known in the art, as well as specific adaptations thereof to accommodate the detection and quantification of various genetic phenomena, as evidenced by the U.S. patents and publications cited above.

The biological samples utilized in the method of the present invention may be obtained from a variety of sources. As noted above, the specific source organism, as well as the location of sampling on or in the organism may be determined by one of ordinary skill in the art using a variety of factors, such as a specific result sought. For example, testing to determine the presence of trisomy 21 (i.e. Down Syndrome) in an unborn fetus may utilize samples from the amniotic fluid of the mother, or samples from the tissue or blood of the fetus.

In one aspect of the present invention, the biological sample may be obtained from epithelium of the oral cavity. In another aspect, the sample may be obtained from blood, or the serum thereof. In another aspect, the sample may be obtained from hair. In yet another aspect, the sample may be obtained from skin or nails. In a further aspect, the sample may be obtained from saliva, or other non-blood bodily fluids. Moreover, the sample may be obtained from an individual displaying certain symptoms or conditions, for example, the sample may be obtained from a woman who is pregnant. In one aspect, the sample may be obtained from the amniotic fluid of a pregnant woman. In addition, the sample may be taken from a source likely to contain specific genetic material required for the desired analysis, for example, from chorionic villi, products of conceptions, such as a fertilized zygote, an embryo, a fetus, neonatal whole blood, and paraffin embedded tissues.

According to the method of the present invention, it is desirable for a sample to contain alleles that are made heterozygous by at least a single nucleotide polymorphism (SNP). As indicated above, derivative melting curves differentiate two alleles by the difference in the thermodynamic stability of the bonding between the allele and a fluorescent hybridization probe. Typically, a pair of probes are used in accordance with the well-known fluorescence resonance energy transfer (FRET) method, one probe being an anchor and donor probe, and a second being a reporter and acceptor probe. However, in some aspects single probe systems may be used. Fluorescence occurs only while the probes are attached to the allele, and fluorescence loss indicates that the probe has denatured from the allele. In other systems, fluorescence occurs only while the probes are denatured and fluorescence loss indicates hybridization. As a result, the temperature (Tm) at which the probe denatures from the allele and the fluorescence signal is lost (or gained), identifies each allele. Therefore, if the alleles being tested are homozygous, fluorescent signals for the alleles are lost (or gained) simultaneously, and a single derivative peak is quantitated. To this end, for quantification of homozygous alleles it is necessary to employ an artificial control or competitor. By contrast, the use of heterozygous alleles, as employed by the present method provides an internal control for the assay, and eliminates the need for an external or artificially created control or competitor, as is required for quantification of homozygous alleles.

A wide variety of SNPs having specific loci may be used as part of the panel of SNPs employed by the present invention. Moreover, the number of SNPs included in the panel may vary. Again, the specific selection of SNPs may depend on a number of criteria that can be determined by one of ordinary skill in the art in preparing to make an allele quantification analysis. For example, when aneuploidy of chromosome 21 is to be tested, SNPs having loci on chromosome 21 may be selected. Numerous SNPs have been mapped along chromosome 21. Public databases collecting these SNPs, as well as others have been established and are readily accessible through a several internet sources.

However, in one aspect of the invention, the target SNPs may each have a heterozygocity index (H.I.) of greater than about 30%. In another aspect, each of the target SNPs may have a H.I. of greater than about 50%. In a further aspect of the invention, each of the target SNPs may have a H.I. of greater than about 60%. In yet another aspect, the panel of the target SNPs may provide at least one heterozygous loci in at least about 95% of a random population. Further, while the panel of SNPs may include any number of SNPs, in one aspect, the panel may include at least 3 different SNPs. In a further aspect, the panel may include at least 4 SNPs. In another aspect, the panel may include at least 6 different SNPs. In yet another aspect, the panel may include more than 6 different SNPs.

As recited above, a wide variety of SNPs may be included in the panel depending on what type of aneuploidy is being analyzed. The loci of a number of SNPs rendering a pair of alleles heterozygous are known. However, in one aspect, the panel of SNPs may include SNPs selected from the group consisting of G22980 (H.I. 49%), G42972 (H.I. 53%), WI-16196 (H.I. 49%), WIAF-2643 (H.I. 49%), WAIF-899 (H.I. 53%), WAIF-1538 (H.I. 47%), WAIF-2215 (H.I. 30%), WAIF-1882 (H.I. 46%), WAIF-1943 (52%), and mixtures thereof. Notably, WAIF-1882 and WAIF-1943, are localized in the DSCR region of chromosome 21, which is thought to be the 2.5 Mb region of from 21q22.1–21q22.3.

Referring now to FIG. 1, is shown a basic concept of the method of the present invention. Chromosomes having alleles made heterozygous by at least one SNP are shown. Heterozygocity of alleles is represented by a gray filled circle on the one chromosome and a black filled circle on the other. As can be seen, one sample contains the proper number of alleles for a diploid organism (i.e. two), while the other samples are trisomic and contain three alleles. Biological samples containing the heterozygous alleles shown are amplified an analyzed using a melting curve analysis in accordance with one aspect of the present invention to produce the corresponding peak area ratios shown. Particularly, the normal diploid sample produced a peak area ratio of approximately 1.0, while the trisomic samples produced a peak area ratio of either approximately 2.0 or 0.5, depending on which extra allele is present.

Measurement and quantification of the melting curve data obtained for a given sample are typically carried out by the LightCycler® Data Analysis software. A data curve is generated by the software using the fluorescence readings measured as a function of temperature, and the negative derivative of the melting curve is used to convert the data into a Gaussian peaks with a quantifiable area (i.e. area under the curve, or "AUC").

It is to be noted that the examples provided below are merely illustrative of specific embodiments for images and methods in accordance with invention disclosed herein, and no limitation thereon is to be inferred thereby.

EXAMPLES

In each of the below-listed examples, the following protocol was used for preparing samples to be analyzed. DNA was extracted by conventional methods from fixed cell pellets (methanol/acetic acid; 3:1) or from amniocytes grown in 25 $cm^2$ cell culture flask. Both types of cells were obtained from the cytogenetics laboratory (University of Utah). DNA was extracted either with a PUREGENE DNA isolation kit for 3 to 5 million fixed cells (Gentra, www-.gentra.com) or on the MagNa Pure LC instrument (Roche Biochemicals) using the MagNa Pure LC DNA Isolation Kit I (Roche Biochemicals). For fixed cells, 2 successive washes were performed with 1XPBS (Ambion, www.ambion.com) prior to extraction. DNA was eluted in 20–50 microliters (ul) of elution buffers.

The following reaction conditions were used for all PCR amplifications required for the Examples recited below. For each SNP, 1 ul of genomic DNA was added to a reaction mixture containing 0.5 uM of each Forward and Reverse PCR primer, 0.2 uM of each Reference (rf) and Anchor (an) hybridization probe, 2 mM MgCl2, 50 mM Tris (pH 8.3), 500 mg/ml bovine serum albumin (buffer #1771, Idaho Technology), 0.2 mM of each dNTPs, 0.4 units of AmpliTaq polymerase blocked with TaqStart antibody (Clontech). The 10 ul reaction mixture was loaded into glass capillary tubes and a LightCycler® instrument (Roche Biochemicals). The following conditions were used for the reaction: 94° C. for 2 seconds, 60° C. for 10 seconds and 72° C. for 15 seconds for 45 cycles. Programmed transition rates were 20° C./second from denaturation to annealing and from extension to denaturation and 2° C./second from annealing to extension.

For each of the Examples set forth below, the amplification cycles as described above, were followed by three consecutive melting cycles. For each melting cycle, the reaction mixture was raised to a temperature of 95° C. for 10 seconds in order to allow DNA to denature, then cooled to 40° C. and held for 120 seconds to allow annealing of the denatured DNA with respective fluorescent probes. The temperature was then raised to 80° C. with a transition rate of 0.1 second/° C. during the first melting cycle, 0.2 second/° C. in the second melting cycle and 0.3 second/° C. in the third melting cycle. Fluorescence was monitored constantly during the melts. Fluorescence versus temperature plots were converted into derivative fluorescent curves with respect to temperature (−dF/dT) for easy visualization of the melting peaks.

The best results for having equal melting peaks in normal DNA were obtained when 25 to 32 reaction tubes were amplified in a single experiment and the following melting cycles were used: WI-16196 was analyzed using the second melting cycle (0.2 second/° C.), with background correction analysis (with the window of temperature analyzed from 44° C. to 66° C. WIAF-899 was analyzed using the first or the second melting cycle, background was corrected and window of temperature was 46–73° C. WIAF 1538 and WIAF 2215 were analyzed using the first melt condition (0.1 second/° C.). Temperatures from 54 to 72° C. for WIAF 1538 and 47 to 77° C. for WIAF 2215 were analyzed. The ratio of both peaks was determined using an excel spread sheet. A known normal DNA was concurrently analyzed in each run and the peak ratio from this sample was used to normalize experimental sample peak ratios.

Example 1

Selection of SNPS

Figure 2:
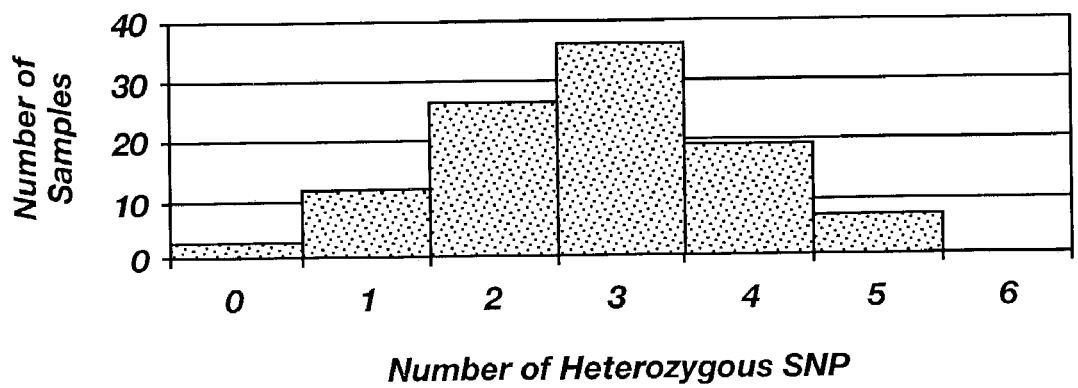
FIG. 2 depicts the heterozygocity index of a selected panel of target SNPs.

A number of SNPs known to have loci on chromosome 21 were selected for Heterozygocity Index (H.I.) testing. The HI is the percent of heterozygotes found in a specific population. One hundred samples were tested according the above-recited protocol to determine the number of heterozygotes for each SNP. As a minimum selection criteria for inclusion in the panel, each SNP was required appear in at least 30 out of 100 thus rendering the alleles thereof heterozygous at the designated loci (i.e. H.I.≧0.30). In the 100 samples tested, more than 90% were found to be heterozygous for 1 or more of the selected SNPs. For clinical testing, ideally two SNPs should be present to detect trisomies. In the 100 samples tested, more than 85% were heterozygous for two or more of the selected SNPs. A graphical representation of the data generated for the tested SNPs is shown in FIG. 2. A panel of six SNPs meeting the above-recited criteria are shown in FIG. 2. The name of each of the selected SNPs in the panel are presented in Table I:

TABLE I

Panel of Target SNPs

| SNP name |
| --- |
| WIAF-2643 |
| WIAF-899 |
| WIAF-1538 |
| WIAF-2215 |
| WIAF-1882 |
| WIAF-1943 |

Example 2

Heterozygocity of SNPs in Trisomic Samples

Thirty eight biological samples known to be trisomic for chromosome 21 were tested using the above-recited protocols to determine how many were heterozygous for the four selected SNPs of the panel in Example 1. The primer sequences and hybridization probes used are set forth in Table II. The sequences of the PCR Primers were available in the SNPs data base listed in Table I. PCR primers were made by the DNA-Peptide Core facility at the University of Utah. Hybridization Probes were designed to allow detection of the SNP following the guidelines described in Lyon E. 2001. *Exp. Rev. Mol. Diag.* 1 (1), 17–26, hereby incorporated by reference. Hybridization Probes were made by Idaho Technology or by Biosearch Technologies using fluoroscein (Biogenix), LCRed640 and LCRed705 (Roche Biochemicals) as the fluorescent labels.

TABLE II

Primer Sequences and Hybridization Probes Used for Detection of Target SNPS

| SNP name | Primer sequence | Hybridization probes |
| --- | --- | --- |
| WIAF 2643 | Forward: AACCCAGTGTGGGAGGAGAA (SEQ ID No. 1) Reverse: GTGGTGCTGTGGGCTAG (SEQ ID No. 2) | Rf-F: CAGAATAAATAGAACAGTAGAATG-F (SEQ ID No. 3) An-705: LCRed705-TACAGATGGGTAATTACACATGTAAATGAGCTC-ph (SEQ ID NO. 4) |
| WIAF-899 | Forward: CAGGCAGGACTTCAGTGTCA (SEQ ID No. 5) Reverse: GTCATCTGGGACAGGTCACC (SEQ ID No. 6) | Rf-F: TTCCTGTTCCACGAAGAGGAC-F (SEQ ID No. 7) An-640: LCRed640-TTTTGTTCACAATTGGATCACAATGCAGAGGAGTCTGTT-ph (SEQ ID No. 8) |
| WIAF-1538 | Forward: TGTTTGTGTTCCAGCCACAT (SEQ ID No. 9) Reverse: CTCTCAGTTAGCAGCTGGGC (SEQ ID No. 10) | Rf-F: F-CCAATGTTATGTCGAAACTGCATTGTAAAAAG-ph (SEQ ID No. 11) An-640: GCGCACCATTCATCATTTAGGCTTGTGGTTTGTTGTTTACTCT-LCRed64O (SEQ ID No. 12) |
| WIAF-2215 | Forward: GGCTCACAAACATCCAC (SEQ ID No. 13) Reverse: CATCAAAGCACCTGTCG SEQ ID No. 14) | Rf-640: TGGTCCCCCTGCCGAGGG-LCRed640 (SEQ. ID No. 15) An-F: F-GTGCGGCCTCTGCAAGGTTCGGGGGTGGCTTCGTTTGCCTGG-Ph (SEQ ID No. 16) |
| WIAF-1882 | Forward: TTTTTTGGCTTGTCTGCAGA (SEQ ID No. 17) Reverse: CAGTGAGCCAGCACTCTTGG (SEQ ID No. 18) | Rf-640: LCRed640-GAGGCAGCGCTTACAGGAG-ph (SEQ ID NO. 19) An-F: CCCAAGTGCACACTAGGCAATGTAAGCTCC-F (SEQ ID No. 20) |

TABLE II-continued

Primer Sequences and Hybridization Probes Used for Detection of Target SNPS

| SNP name | Primer sequence | Hybridization probes |
|---|---|---|
| WAIF-1943 | Forward: TTTTTAACGAAATCTCACTACTGCA (SEQ ID No. 21) Reverse: CTATGCACCATGTACTGTTCTAAGC (SEQ ID No. 22) | Rf-640: GCTAATGAATGCACAGAGTAT-F (SEQ ID No. 23) An-F LCRed705-GCCTGCAAAATAATAATTGAGATTCTATTTTTAAG-ph (SEQ ID No. 24) |

All sequences are given in the conventional 5' to 3' orientation. Fluorophore labels [F (fluorescein), LCRed640 and LCRed705] synthesized at the 5' or the 3' end of the probes are indicated and separated from the oligonucleotide sequence by a dash. Phosphate groups (ph) used to block the 3'end of oligonucleotides are indicated.

Figure 3:
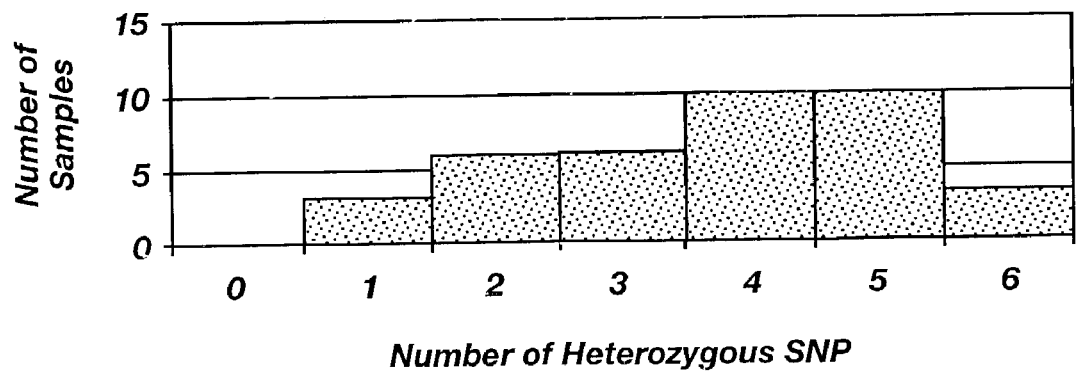
FIG. 3. is a graphical representation of the heterozygocity of the target SNPs of FIG. 2 in trisomic samples.

As can be seen from the graph in FIG. 3, only one of the 33 samples was homozygous at all alleles tested (i.e. contained none of the SNPs in the panel), and was therefor considered non-informative. However, approximately 75% (25/33) of the samples had at least two heterozygous SNPs and therefore provided informative data.

Example 3

Figure 4:
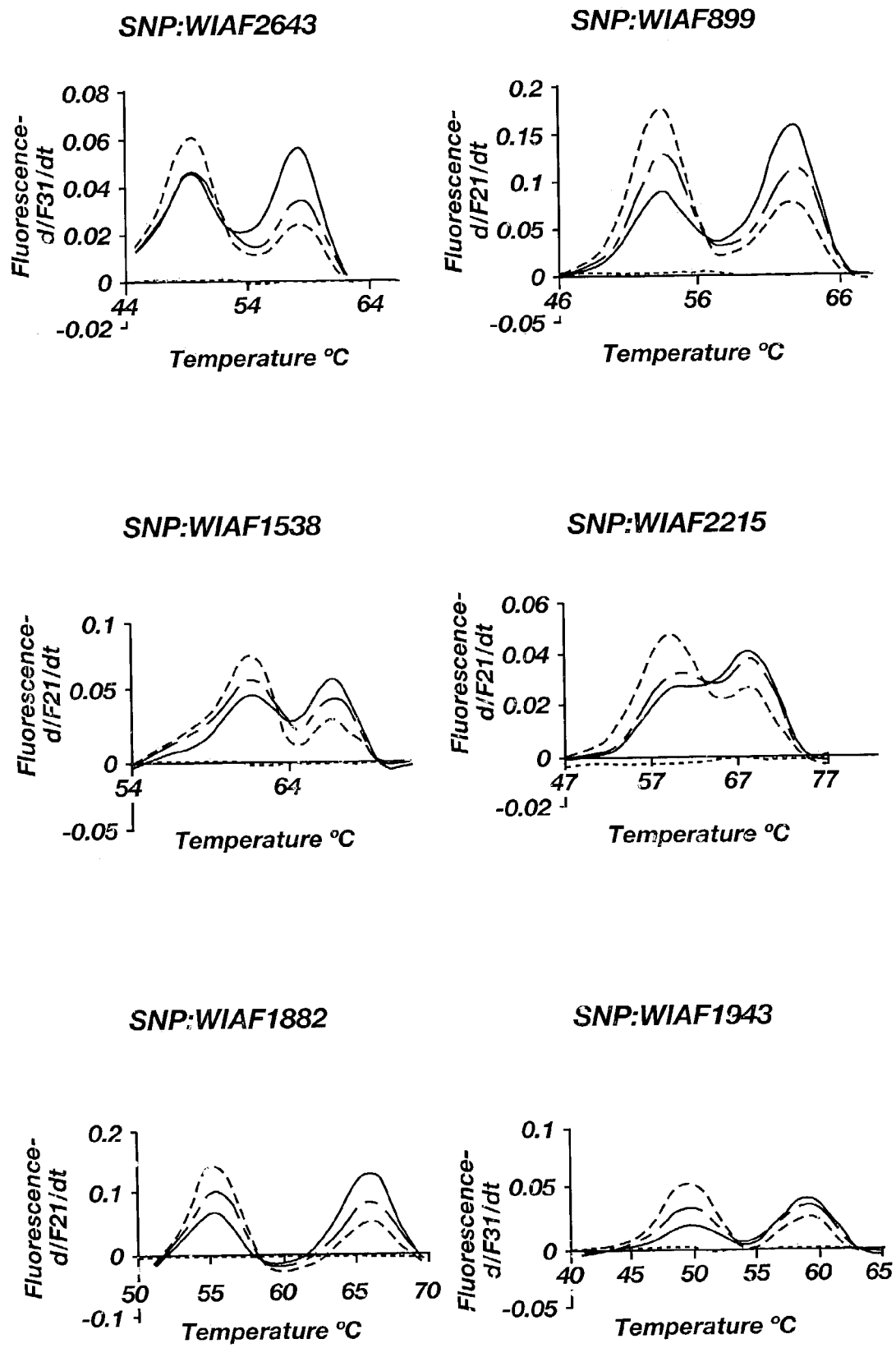
FIG. 4. shows the melting peaks obtained for both normal and trisomic samples using the target SNPs of FIG. 2.

Using the SNPs and protocols of Example 2, a number of melting peaks were generated for both normal and trisomic biological samples, for each of the four SNPS tested. FIG. 4 illustrates the melting peaks of both normal and trisomic samples for each SNP. As can be seen, the normal samples typically yield a near 1:1 area under the curve ratio of allele peaks, whereas the trisomic samples yield either a 1:2 or 2:1 ratio.

Example 4

Figure 5:
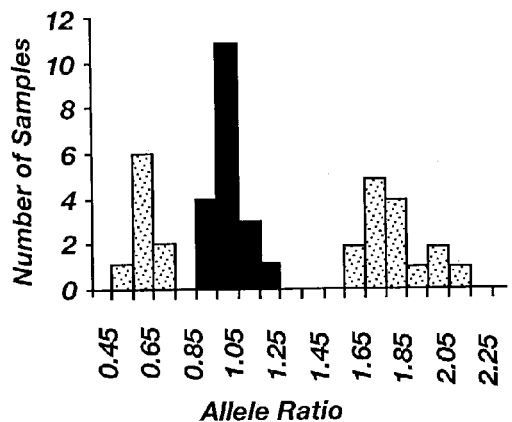
FIG. 5. is a graphical representation of the peak ratios obtained for both normal and trisomic samples using the target SNPs of FIG. 2.
Figure 5:
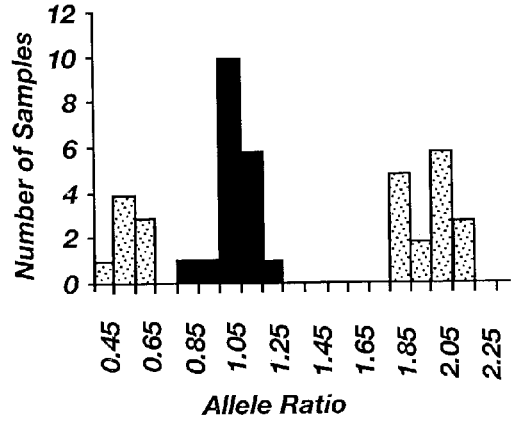
Figure 5:
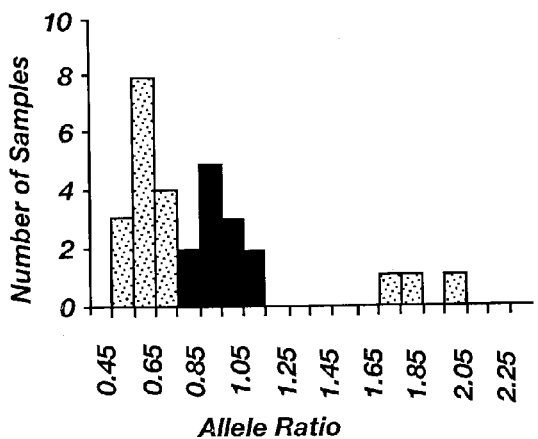
Figure 5:
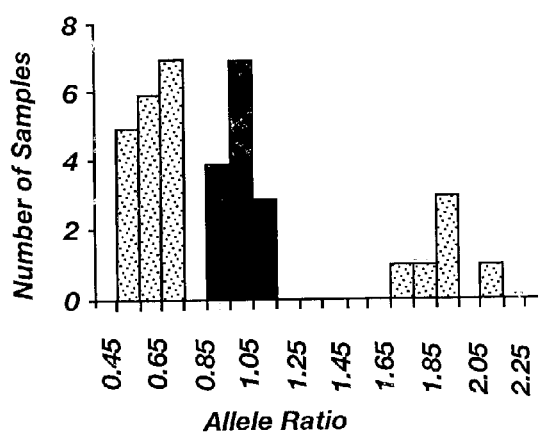

Normal and Trisomy 21 samples were tested using the panel of six SNPs and protocols recited in Example 2. The AUC ratios were determined for heterozygous samples, and the results for four of the SNPs are presented in FIG. 5. Peak ratios were grouped by values of 0.1 intervals. The numbers on the X axes of the histograms represent the highest value of the interval. The peak ratios for normal samples ranged from 0.75 to 1.35, while the ratios for Trisomy samples ranged from 0.35–0.75 (for samples with an extra copy of allele #1) and 1.5–2.25 (for samples with an extra copy of allele #2). No overlap between the ratios was seen between normal and trisomic samples for 3 of the selected SNPs. Based on limited data, a potential overlap was seen in one trisomic sample (with an extra allele #2) for WIAF2215.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for identifying chromosomal aneuploidy in a biological sample, comprising the steps of:
   a) providing a biological sample from an embryo or a fetus containing heterozygous alleles having a single nucleotide polymorphism (SNP) and heterozygous alleles acting as a hybridization quantification internal control;
   b) selecting a panel of at least 3 different target SNPs each having a heterozygocity index of greater than about 30% and having loci sufficiently distributed throughout chromosome 21 to allow detection of chromosomal trisomy, partial trisomy, and chromosomal breakpoint locations;

c) hybridizing target SNPs contained in the heterozygous alleles with fluorescent hybridization probes;

d) measuring hybridization as a function of fluorescence and temperature; and e) quantifying hybridization as a ratio of heterozygous alleles present in the biological sample and categorizing each ratio as indicative of either trisomic or non-trisomic alleles.

2. The method of claim 1, wherein said target SNPs each has a heterozygocity index of greater than about 50%.

3. The method of claim 1, wherein said panel of target SNPs provides at least one heterozygous loci in at least about 95% of a random population.

4. The method of claim 1, wherein the target SNPs on chromosome 21 include loci in an area of the chromosome of from about 21q22.1 to about 21q22.3.

5. The method of claim 1, wherein the distribution of target SNPs is sufficient to distinguish between chromosomal trisomy and partial trisomy.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<221> NAME/KEY: primer_bind
<223> OTHER INFORMATION: Forward primer sequence used in PCR

<400> SEQUENCE: 1
aacccagtgt gggaggagaa                                                 20

<210> SEQ ID NO 2
<211> LENGTH: 17
<212> TYPE: DNA
<213> ORGANISM: Artificial Sequence
<220> FEATURE:
<221> NAME/KEY: primer_bind
<223> OTHER INFORMATION: Reverse primer sequence used in PCR
```

-continued

```
<400> SEQUENCE: 2
gtggtgctgt gggctag                                                17

<210> SEQ ID NO 3
<211> LENGTH: 24
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 3
cagaataaat agaacagtag aatg                                        24

<210> SEQ ID NO 4
<211> LENGTH: 33
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 4
tacagatggg taattacaca tgtaaatgag ctc                               33

<210> SEQ ID NO 5
<211> LENGTH: 20
<212> TYPE: DNA
<213> ORGANISM: Artificial Sequence
<220> FEATURE:
<221> NAME/KEY: primer_bind
<223> OTHER INFORMATION: Forward primer sequence used in PCR

<400> SEQUENCE: 5
caggcaggac ttcagtgtca                                             20

<210> SEQ ID NO 6
<211> LENGTH: 20
<212> TYPE: DNA
<213> ORGANISM: Artificial Sequence
<220> FEATURE:
<221> NAME/KEY: primer_bind
<223> OTHER INFORMATION: Reverse primer sequence used in PCR

<400> SEQUENCE: 6
gtcatctggg acaggtcacc                                             20

<210> SEQ ID NO 7
<211> LENGTH: 21
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 7
ttcctgttcc acgaagagga c                                           21

<210> SEQ ID NO 8
<211> LENGTH: 39
<212> TYPE: DNA
<213> ORGANISM: Artificial Sequence
```

-continued

```
<220> FEATURE:
<221> NAME/KEY: misc_binding
<223> OTHER INFORMATION: Hybridization probe used in PCR melting point
      analysis

<400> SEQUENCE: 8
ttttgttcac aattggatca caatgcagag gagtctgtt                         39

<210> SEQ ID NO 9
<211> LENGTH: 20
<212> TYPE: DNA
<213> ORGANISM: Artificial Sequence
<220> FEATURE:
<221> NAME/KEY: primer_bind
<223> OTHER INFORMATION: Forward primer sequence used in PCR

<400> SEQUENCE: 9
tgtttgtgtt ccagccacat                                              20

<210> SEQ ID NO 10
<211> LENGTH: 20
<212> TYPE: DNA
<213> ORGANISM: Artificial Sequence
<220> FEATURE:
<221> NAME/KEY: primer_bind
<223> OTHER INFORMATION: Reverse primer sequence used in PCR

<400> SEQUENCE: 10
ctctcagtta gcagctgggc                                              20

<210> SEQ ID NO 11
<211> LENGTH: 32
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 11
ccaatgttat gtcgaaactg cattgtaaaa ag                                32

<210> SEQ ID NO 12
<211> LENGTH: 43
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 12
gcgcaccatt catcatttag gcttgtggtt tgttgtttac tct                    43

<210> SEQ ID NO 13
<211> LENGTH: 17
<212> TYPE: DNA
<213> ORGANISM: Artificial Sequence
<220> FEATURE:
<221> NAME/KEY: primer_bind
<223> OTHER INFORMATION: Forward primer sequence used in PCR

<400> SEQUENCE: 13
ggctcacaaa catccac                                                 17
```

```
<210> SEQ ID NO 14
<211> LENGTH: 17
<212> TYPE: DNA
<213> ORGANISM: Artificial Sequence
<220> FEATURE:
<221> NAME/KEY: primer_bind
<223> OTHER INFORMATION: Reverse primer sequence used in PCR

<400> SEQUENCE: 14
catcaaagca cctgtcg                                                  17

<210> SEQ ID NO 15
<211> LENGTH: 18
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 15
tggtccccct gccgaggg                                                 18

<210> SEQ ID NO 16
<211> LENGTH: 42
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 16
gtgcggcctc tgcaaggttc gggggtggct tcgtttgcct gg                      42

<210> SEQ ID NO 17
<211> LENGTH: 20
<212> TYPE: DNA
<213> ORGANISM: Artificial Sequence
<220> FEATURE:
<221> NAME/KEY: primer_bind
<223> OTHER INFORMATION: Forward primer sequence used in PCR

<400> SEQUENCE: 17 tttttttggct tgtctgcaga                                              20

<210> SEQ ID NO 18
<211> LENGTH: 20
<212> TYPE: DNA
<213> ORGANISM: Artificial Sequence
<220> FEATURE:
<221> NAME/KEY: primer_bind
<223> OTHER INFORMATION: Reverse primer sequence used in PCR

<400> SEQUENCE: 18
cagtgagcca gcactcttgg                                               20

<210> SEQ ID NO 19
<211> LENGTH: 19
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis
```

-continued

```
<400> SEQUENCE: 19
gaggcagcgc ttacaggag                                                    19

<210> SEQ ID NO 20
<211> LENGTH: 30
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 20
cccaagtgca cactaggcaa tgtaagctcc                                        30

<210> SEQ ID NO 21
<211> LENGTH: 25
<212> TYPE: DNA
<213> ORGANISM: Artificial Sequence
<220> FEATURE:
<221> NAME/KEY: primer_bind
<223> OTHER INFORMATION: Forward primer sequence used in PCR

<400> SEQUENCE: 21
tttttaacga aatctcacta ctgca                                             25

<210> SEQ ID NO 22
<211> LENGTH: 25
<212> TYPE: DNA
<213> ORGANISM: Artificial Sequence
<220> FEATURE:
<221> NAME/KEY: primer_bind
<223> OTHER INFORMATION: Reverse primer sequence used in PCR

<400> SEQUENCE: 22
ctatgcacca tgtactgttc taagc                                             25

<210> SEQ ID NO 23
<211> LENGTH: 21
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 23
gctaatgaat gcacagagta t                                                 21

<210> SEQ ID NO 24
<211> LENGTH: 35
<212> TYPE: DNA
<213> ORGANISM: Artificial Sequence
<220> FEATURE:
<221> NAME/KEY: misc_binding
<223> OTHER INFORMATION: Hybridization probe used in PCR melting point
      analysis

<400> SEQUENCE: 24
gcctgcaaaa taataattga gattctattt ttaag                                  35
```